United States Patent [19]

Belcher et al.

[11] Patent Number: 4,898,881

[45] Date of Patent: Feb. 6, 1990

[54] DRY MICROBIOCIDAL COMPOSITION CONTAINING AN ETHYLENE BIS-DITHIOCARBAMATE SALT

[75] Inventors: James H. Belcher, Chattanooga; Girish K. Patel, Hixson, both of Tenn.

[73] Assignee: Alco Chemical Corporation, Tenn.

[21] Appl. No.: 181,415

[22] Filed: Apr. 14, 1988

[51] Int. Cl.[4] .................. A61K 31/27; A01N 47/10
[52] U.S. Cl. ................................................ 514/481
[58] Field of Search ......................................... 514/481

[56] References Cited

U.S. PATENT DOCUMENTS

| | | | |
|---|---|---|---|
| 1,610,216 | 12/1926 | Elley | 524/332.7 |
| 1,972,961 | 9/1934 | Tisdale et al. | 514/478 |
| 2,317,765 | 4/1943 | Hester | 514/483 |
| 2,545,948 | 3/1951 | Flenner | 514/483 |
| 2,857,680 | 10/1958 | Beinfest et al. | 34/15 |
| 2,857,681 | 10/1958 | Beinfest et al. | 34/15 |
| 2,992,161 | 7/1961 | Flenner | 514/494 |
| 3,050,439 | 8/1962 | Nemec et al. | 514/483 |
| 3,050,552 | 8/1962 | Nemec et al. | 260/13.5 |
| 3,085,042 | 4/1963 | Luginbuhl | 514/483 |
| 3,449,386 | 6/1969 | Chiffert et al. | 556/6 |
| 3,521,371 | 7/1970 | Kraft | 34/15 |
| 3,523,960 | 8/1970 | Lehureau | 556/6 |
| 3,856,836 | 12/1974 | Van Den Boogaart et al. | 556/2 |
| 3,869,486 | 3/1975 | Van den Boogaart et al. | 260/429 K |
| 4,079,146 | 3/1978 | Miller et al. | 514/481 |
| 4,185,113 | 1/1980 | Virrion et al. | 514/583 |
| 4,217,293 | 8/1980 | Adams | 556/2 |

OTHER PUBLICATIONS

Marsh; R. W. (1938) Ann. Appl. Biol.
Dimond; A. E. et al. (1943) Phytopathology.
Heuberger, J. W. et al. (1943) Phytopathology.
G. D. Thorn et al., "The Dithiocarbamates and Related Compounds", Elsevier Pub. Co., N.Y. (1962).

*Primary Examiner*—Douglas W. Robinson
*Assistant Examiner*—Zohteh A. Fay
*Attorney, Agent, or Firm*—Howson & Howson

[57] ABSTRACT

A stable dry microbiocidal composition is disclosed which consists of partially anhydrous alkaline salts of ethylene bis-dithiocarbamate and alkaline salts of dimethyldithiocarbamate. This dry composition has a temperature of combustibility over 170° C. Methods for preparing the composition are also described.

12 Claims, No Drawings

DRY MICROBIOCIDAL COMPOSITION CONTAINING AN ETHYLENE BIS-DITHIOCARBAMATE SALT

The present invention relates generally to novel non liquid compositions containing alkaline salts of ethylene bis-dithiocarbamate. More particularly, the invention relates to a surprisingly stable dry composition of an ethylene bis-dithiocarbamate salt and a dimethyldithiocarbamate salt for microbiocidal use.

BACKGROUND OF THE INVENTION

As a class of chemicals, dithiocarbamates and methods for their synthesis have been known for over a hundred years. The alkaline earth-salts of dithiocarbamates, such as sodium and potassium, and the heavy-metal salts of dithiocarbamates, such as zinc and magnesium, have found wide-spread use in agriculture and industry as important microbiocidal and fungicidal compositions. [See, e.g., U.S. Pat. No. 1,972,961] The sodium and potassium salts of dithiocarbamic acids have primarily been used in liquid form, while the heavy metal zinc and magnesium salts are presently used as dry powders dispersed in water or in water-in-oil emulsions.

One particularly valuable microbiocidal product that has been on the market for many years is a liquid combination of equal parts by weight of sodium dimethyldithiocarbamate (referred to hereafter as "SDDC") and disodium ethylene bis-dithiocarbamate referred to hereafter as ("NABAM") (30%, by weight, total active ingredients). This liquid material is used in many industries for controlling the growth of bacteria, yeast and fungi, such as those found in industrial recirculating water cooling towers, air washers, evaporative condensers, pulp and paper mills, drilling fluids, secondary and tertiary petroleum recovery, cane and beet sugar mills, and the like. This compound has also been used for controlling the growth of algae in some of these applications.

The chemical instability of compounds containing ethylene bis-dithiocarbamate (referred to hereafter as "EBDC") was recognized at about the time of the discovery of their use as fungicides. [See, e.g. A. E. Dimond et al., Phytopathology (1943); U.S. Pat. No. 2,317,765]. This instability manifests itself during manufacture and storage of liquid or dry products containing disodium ethylene bis dithiocarbamate ("NABAM"). For example, J. W. Heuberger, et al, Phytopathology (1943) reported the use of a zinc sulfate—lime mixture to stabilize the chemical instability associated with EBDC salts. Various other means have been proposed to stabilize NABAM. For example, U.S. Pat. No. 3,449,386 discusses using 1,8,3,6-diendomethylene-1,3,6,8-tetrazacyclodecane to stabilize the heavy metal salt, manganous ethylene bis dithiocarbamate. Cuprous compounds have also been employed to stabilize heavy metal salts of zinc, manganese, or iron ethylene bis-dithiocarbamate, according to U.S. Pat. No. 3,523,960. Similarly aqueous formaldehyde (U.S. Pat. No. 3,856,836) and cinnamic aldehyde (U.S. Pat. No. 4,185,113) have been added to precipitated manganese and zinc salts of EBDC to provide enhanced chemical stability. U.S. Pat. No. 4,217,293 discloses the blending of paraformaldehyde with dry manganese ethylene bis dithiocarbamate [MANEB] for stabilizing purposes.

These methods of imparting stability to compounds containing EBDC involve the use of a variety of additives to stabilize the heavy metal salts of EBDC. The disadvantage of these approaches to stabilizing metal salts of ethylene bis-dithiocarbamate are that these additives, though they may impart stabilizing properties, are also diluents or adulterants of the microbiocidal or fungicidal activity of the compounds containing EBDC.

Few efforts have focused on imparting stability to the presently most useful EBDC for microbiocidal use, i.e., the disodium EBDC, or NABAM. U.S. Pat. Nos. 3,050,439 and 3,050,532 disclose methods for producing anhydrous NABAM by spray drying method. The disadvantages of the spray drying process of '439 are that the process must be under very careful control or decomposition will result; and that, once produced, the anhydrous salt must be kept away from moisture or it will revert to the hydrate, decomposing in the process.

There remains a continuing need for improved microbiocidal compounds for a variety of industrial uses which are capable of efficiently controlling growth of microorganisms and yet can be readily manufactured and used in industry.

SUMMARY OF THE INVENTION

As one aspect of the present invention, a stable dry microbiocidal composition is provided containing as a major component, a partially anhydrous alkaline salt of ethylene bis-dithiocarbamate. This composition is surprisingly characterized by a significantly higher temperature of composition than that possessed by anhydrous NABAM or prior art compositions containing alkaline EBDC's, particularly NABAM. Among the alkaline salts useful in this composition are the disodium, calcium and potassium salts of EBDC.

This composition also contains an alkaline salt of dimethyldithiocarbamate as an additive to the ethylene bis-dithiocarbamate salt. This dimethyldithiocarbamate salt also has microbiocidal properties and unexpectedly imparts stabilizing properties to the dry EBDC. Alkaline salts of dimethyldithiocarbamate for use in this composition can include sodium, potassium and calcium salts.

Surprisingly, the chemical stability of compositions containing an alkaline salt of ethylene bis-dithiocarbamate can be increased and the manifestations of decomposition decreased by the addition of an alkaline salt of dimethyldithiocarbamate. In addition to the advantages imparted by stabilizing the combustibility of the dry EBDC, the dimethyldithiocarbamate salts are themselves employed as microbiocides, and their addition to the EBDC does not "dilute" the microbiocidal effect of the total dry composition, as would the addition of inert materials or other components previously used in attempts to stabilize EBDC.

The novel composition is thus characterized by ease of manufacture and storage, and is capable of all the microbiocidal functions of its liquid counterparts, e.g. known microbiocides containing liquid NABAM and SDDC. Thus, the stable dry composition may be used in controlling the growth of algae, bacteria, yeast and fungi in a variety of industrial uses.

Another aspect of the invention involves a method for preparing the microbiocidal composition described above. The steps of the method involve subjecting a liquid mixture of the two salts to a vacuum of at least 23 inches Hg under a temperature of between 105°–116° C., for a time sufficient to dry the mixture to a pale powder. The vacuum may be greater than 23 inches Hg, but must be low enough to keep the temperature within the stated range. The resulting product is a dry powder stable to combustion up to a temperature of at least 170° C. If desired, each component may be dried under these conditions individually and mixed together as two dry powders to form the stable composition.

Further aspects and advantages of the present invention will become apparent upon consideration of the following detailed description of presently preferred embodiments thereof.

DETAILED DESCRIPTION OF THE INVENTION

A dry stable microbiocidal composition according to the present invention contains primarily an alkaline salt of ethylene bis-dithiocarbamate stabilized in dry form by a alkaline salt of dimethyldithiocarbamate. The ratio of the EBDC to the dimethyldithiocarbamate salt in the composition is between 4:1 and 1:4 by weight. Most desirably, the ratio of the components of the composition is 1:1 by weight. A preferred composition is formed of 1 part by weight NABAM to 1 part by weight SDDC.

Such compositions according to the invention have a combustion temperature greater than that of anhydrous forms of the EBDC alone or of known compositions containing EBDC. For example, anhydrous NABAM alone has a combustion temperature of 170° C. Compositions of the present invention have combustion temperatures of greater than 170° C. Combustion temperatures of compositions of the invention may exceed 230° C., depending on the amount of dimethyldithiocarbamate salt present as illustrated in Table I by Sample I9E. This increased combustion temperature enables the dry compositions of the present invention to be stored longer and manufactured with greater ease. Such a dry composition is preferred to a liquid composition of these components because it is more easily handled by its end user than the liquid mixture.

The method of preparing the compositions according to the invention involves preparing the EBDC as the liquid alkaline salt, preferably sodium, in water with an amine and carbon disulfide employing conventional techniques. Similarly, the liquid alkaline salt of dimethyldithiocarbamate is made conventionally. The salts may be prepared individually in liquid form and mixed in a preferred ratio for the drying step or prepared initially in combination in solution.

The method by which the liquid bis-dithiocarbamate and dimethyldithiocarbamate salt compositions are dried to form the composition of the present invention employs very controlled conditions of temperature and vacuum. Preferably, the liquid composition of both salts in a desired ratio is subjected to drying under controlled vacuum and temperature conditions for a time sufficient to render the composition substantially anhydrous. A temperature between about 106° C. to about 115° C. and vacuum of at least 23 inches Hg. minimum are required conditions for this method. While there is no maximum for the vacuum, it must be understood that the lower the vacuum the higher the resulting temperature. Therefore, the vacuum must be in a range wherein the temperature can stay between 106° C. and 115° C. Depending on these selected conditions, the time sufficient to remove all of the water of solution and part of the water of crystalization from the EBDC/dimethyldithiocarbamate salt composition may range from about 0.5 to over 3 hours.

Where the control conditions are appropriate, the product that emerges is fairly stable and stays white over time. If the temperature is not maintained at a proper level, the product will be yellow or it will burn in air. The temperature of blackening or combustion is higher with the mixture of the present invention than with EBDC alone. Consistent conditions for the vacuum drying provide an 80–85% product in which all water of solution and a substantial amount of water of crystalization is removed. Thus, a stable dry, partially anhydrous salt is produced. These results surprisingly contradict U.S. Pat. Nos. 3,050,439 and 3,050,532 which teach that any compound with EBDC less than totally anhydrous is not stable and will decompose.

The tendency toward decomposition of these compositions is theorized to be dependent on temperature and the moisture to which the anhydrous EBDC in the combined dry composition is exposed. The partially anhydrous EBDC of the compositions of this invention does not decompose as readily as anhydrous EBDC. Similarly, the anhydrous combination of the present invention is hydrated but nevertheless is more stable to decomposition than anhydrous EBDC. For some presently unknown reason, the dimethyldithiocarbamate salt component lessens the tendency of the EBDC in the composition to decompose.

The following examples illustrate several compositions of the invention prepared according to the claimed method.

EXAMPLE I

Decomposition Temperature of Compositions of the Invention

A number of compositions according to the invention were made using liquid NABAM and SDDC, prepared using the conventional techniques for liquid compositions. The components of these compositions, designations I9A to I9M, are listed in columns 4 and 5 of Table I.

After calibrating a hot bench melting point apparatus using OMEGA melting point standards, approximately 0.1 gram sample was placed on the hot bench at 5.0° C. intervals and the decomposition temperature of the composition noted after 5 minutes. Also noted was the highest temperature at which no color change occurred. Decomposition was determined to be the temperature at which the sample changed from its starting color to brown or black accompanied by the liberation of noxious fumes. In certain cases, as noted, the sample actually appeared to combust. The highest temperature tested was 250° C.

The composition may also be analyzed after vacuum drying by the conventional Karl Fisher method in which water and an iodine containing reagent are mixed. The iodine containing reagent changes color to determine how much water is in the dried compound. This method is based on an oxidation reduction potential of the resulting compound. It is considered an electrometric or colorimetric measurement of the reagent with water. The Karl Fisher Calculation is closer to the real determination of the amount of water in the composition and this calculation is repeated in Tables I, IIA and IIB.

Table I illustrates the results of this test. The dry compositions containing mixtures of NABAM and SDDC according to the invention are more stable to decomposition than NABAM itself. Evidence of this stabilizing property is shown by the higher decomposition temperatures shown in Table I for samples I9D, I9E, I9F, and I9G. The stabilization increase was demonstrated by the lack of any indication that any part of each of the mixtures was decomposing at the lower temperatures, indicated by samples I9B and I9C.

ing amounts of EBDC sodium salt and a sodium salt of dimethyl dithiocarbamate were placed in heated containers. The temperature of the containers was controlled at 100° C. The humidity was controlled at either 20% relative humidity (R.H.) or 100% R.H. The samples were kept at these conditions for 10 days.

The following Tables IIA and IIB illustrate the results of this test. Samples I9D–I9M have increased sta-

TABLE I

| Sample | Stable to °C. No Color Change | Decomp. Temp °C. | gm EBDC (Sample) | gm SDDC (Sample) | Moisture By (Wt. Loss) | K.F. | Total DTC Purity by Acid Decomp. | Notes |
|---|---|---|---|---|---|---|---|---|
| I 9 A | 185 | 250 | 0 | 100 | (19.1) | 21.8 | 77.5 | |
| I 9 B | 50 | 80 | 100 | 0 | (30.7) | 45.2 | 50.3 | Combustion @ 110° C. |
| I 9 C | 120 | 170 | 100 | 0 | (14.8) | 13.1 | 84.6 | |
| I 9 D | 135 | 220 | 50 (9B) | 50 (9A) | (25.2) | 30.8 | 67.9 | |
| I 9 E | 170 | 230 | 50 (9C) | 50 (9A) | (18.2) | 17.4 | 81.3 | |
| I 9 F | 130 | 215 | 60 (9B) | 40 (9A) | (37.5) | 36.7 | 61.9 | |
| I 9 G | 170 | 220 | 60 (9C) | 40 (9A) | (14.9) | 15.1 | 82.7 | |
| I 9 H | 130 | 200 | 70 (9B) | 30 (9A) | (38.3) | 37.2 | 60.9 | |
| I 9 I | 155 | 215 | 70 (9C) | 30 (9A) | (16.3) | 14.7 | 83.7 | |
| I 9 J | 80 | 120 | 80 (9B) | 20 (9A) | (39.1) | 40.5 | 57.3 | |
| I 9 K | 135 | 205 | 80 (9C) | 20 (9A) | (16.9) | 14.2 | 82.7 | |
| I 9 L | 55 | 85 | 90 (9B) | 10 (9A) | (43.6) | 41.9 | 55.1 | |
| I 9 M | 125 | 190 | 90 (9C) | 10 (9A) | (14.7) | 12.2 | 84.4 | |

EXAMPLE II

Temperature/Humidity Stability Test

An aliquot of approximately 10 grams of each sample as identified in Example I and Table I containing varybility, illustrated by lower amount of weight loss of those samples compared to samples I9B and sample I9C. This increased stability is more apparent when the potential loss which could come from moisture is taken into account.

TABLE II

| | Temperature 100° C., Humidity 100% R.H. | | | | | |
|---|---|---|---|---|---|---|
| | Moisture % | | Beginning Sample Weight | Ending Sample Weight | Weight Loss | |
| Sample | Weight Loss | K.F. | gm | gm | gm (%) | Color change Notes |
| I 9 A | 19.1 | 21.8 | 10.2763 | 10.2029 | 0.0734 (0.71) | No color change |
| I 9 B | 30.7 | 45.2 | 10.7451 | 7.7821 | 2.9630 (27.58) | Lt yellow to Dk brown Strong odor/pressure in bottle |
| I 9 C | 14.8 | 13.1 | 10.3725 | 6.7431 | 3.4294 (33.06) | gray white to black very odorous |
| I 9 D | 25.2 | 30.8 | 9.8973 | 8.6667 | 1.2306 (12.43) | green white to Lt yellow |
| I 9 E | 18.2 | 17.4 | 10.7634 | 9.7902 | 0.9732 (9.04) | white to Lt yellow not much change |
| I 9 F | 37.5 | 36.7 | 10.3631 | 8.3568 | 1.5267 (14.73) | green white to yellow |
| I 9 G | 14.9 | 15.1 | 10.2911 | 9.1889 | 1.1022 (10.71) | white to Dk yellow |
| I 9 H | 38.3 | 37.2 | 10.0371 | 8.8585 | 1.1786 (17.92) | Lt yellow to Dk yellow |
| I 9 I | 16.3 | 14.7 | 10.1077 | 8.5552 | 1.5525 (15.36) | white to brown |
| I 9 J | 39.1 | 40.5 | 10.3102 | 7.6523 | 2.6579 (25.78) | Lt yellow to DK brown |
| I 9 K | 16.9 | 14.2 | 10.4501 | 7.3402 | 3.1099 (29.76) | white to Dk brown |
| I 9 L | 43.6 | 41.9 | 10.6892 | 7.8886 | 2.8006 (26.20) | Lt yellow to black pressure in bottle |
| I 9 M | 14.7 | 12.2 | 10.1357 | 6.9906 | 3.1451 (31.03) | white to black |
| | Temperature 100° C., Humidity 20% R.H. | | | | | |
| | Moisture % | | Beginning Sample Weight | Ending Sample Weight | Weight Loss | |
| Sample | Weight Loss | K.F. | gm | gm | gm (%) | Color change Notes |
| I 9 A | 19.1 | 21.8 | 9.9016 | 9.0976 | 0.8040 (8.12) | No color change |
| I 9 B | 30.7 | 45.2 | 10.3445 | 6.5988 | 3.7457 (36.21) | Lt yellow to yellow |
| I 9 C | 14.8 | 13.1 | 10.1396 | 10.0036 | 0.1360 (1.3413) | white to yellow |
| I 9 D | 25.2 | 30.8 | 10.2719 | 8.0233 | 2.2486 (21,89) | green white to Dk yellow |

TABLE II-continued

| | | | | | | |
|---|---|---|---|---|---|---|
| I 9 E | 18.2 | 17.4 | 9.9374 | 9.6275 | 0.3099 (3.12) | white to very pale yellow |
| I 9 F | 37.5 | 36.7 | 10.4768 | 7.8565 | 2.6203 (25.04) | green white to very pale yellow |
| I 9 G | 14.9 | 15.1 | 10.0021 | 9.6330 | 0.3691 (3.69) | white to yellow |
| I 9 H | 38.3 | 37.2 | 10.6476 | 7.8611 | 2.7865 (26.17) | Lt yellow to yellow |
| I 9 I | 16.3 | 14.7 | 10.2293 | 9.9316 | 0.2977 (2.91) | white to yellow |
| I 9 J | 39.1 | 40.5 | 10.7237 | 7.3099 | 3.4198 (31.89) | Lt yellow to yellow |
| I 9 K | 16.9 | 14.2 | 10.2268 | 10.0079 | 0.2189 (35.78) | white to yellow |
| I 9 L | 43.6 | 41.9 | 9.9873 | 6.4138 | 3.5735 (35.78) | Lt yellow to yellow |
| I 9 M | 14.7 | 12.2 | 10.1902 | 9.9986 | 0.1916 (1.88) | white to yellow |

A composition of the invention is primarily employed as microbiocidal and fungicidal composition for a variety of industrial uses, including all known uses for liquid mixtures of EBDC and sodium dimethyldithiocarbamate. This dry composition may also be used at the concentrations provided for use of the liquid materials. It is also potentially useful in the vulcanization of rubber and in removing metals from waste water. It may be a microbiocidal additive to water supplies of cooling towers and air washers. It may also be employed as a microbiocide in secondary and tertiary oil recovery operations where water is injected into the ground and forced through the pores of rocks. Similarly, these dry compositions may be employed as microbiocides in other fields, e.g. in water based drilling fluids, in water used in grinding and conveying pulp and as a medium for forming a paper web, and in the treatment of sugar cane and sugar beets in sugar production.

Incorporated by reference herein for the purpose of providing background on the uses and use concentrations of the liquid microbiocides containing liquid EBDC is the advertising brochure "Aquatreat Microbiocides" by Alco Chemical Corporation. For example, like the liquid composition of EBDC/SDDC, the dry composition can contain 36, 30% or 9% active mixtures of equal portions of dry EBDC/SDDC. The 30% active mixture may be useful to kill algae, fungi or bacteria at concentrations as low as 2.5 ppm to over 30 ppm.

Numerous other modifications and variations of the invention as above-described are expected to occur to those skilled in the art and consequently only such limitations as appear in the appended claims should be placed thereon.

What is claimed is:

1. A dry water soluble composition for use as a microbiocide comprising a mixture of a sodium or potassium salt of ethylene bis-dithiocarbamate and a sodium or potassium salt of dimethyldithiocarbamate in a weight ratio of between about 4:1 and about 1:4, said composition being free of water of solution and of a substantial amount of water of crystalization and having a temperature of combustion over 170° C.

2. The composition of claim 1 wherein the salt of ethylene bis-dithiocarbamate is disodium ethylene bis-dithiocarbamate.

3. The composition of claim 1 wherein the salt of dimethyldithiocarbamate is sodium dimethyldithiocarbamate.

4. The composition of claim 1 wherein the salt of ethylene bis-dithiocarbamate is disodium ethylene bis-dithiocarbamate and wherein the salt of dimethyldithiocarbamate is sodium dimethyldithiocarbamate.

5. The composition of claim 1 wherein said weight ratio is about 1:1.

6. The composition of claim 4 wherein said weight ratio is about 1:1.

7. The composition of claim 1 wherein said temperature of combustion ranges from 200°-250° C.

8. A method for preparing a stable dry water soluble microbiocidal composition comprising the steps of subjecting a liquid mixture of a sodium or potassium salt of ethylene bis-dithiocarbamate and a sodium or potassium salt of dimethyldithiocarbamate in a weight ratio of from 4:1 to 1:4 to vacuum drying at a temperature of between 106° C. and 115° C. with a minimum vacuum of at least 23 inches of mercury for a time sufficient to remove all water of solution and a substantial amount of water of crystalization and provide a dry powder characterized by a pale color, which is stable to combustibility to temperatures over 170° C.

9. The method of claim 8 wherein the salt of ethylene bis-dithiocarbamate is disodium ethylene bis-dithiocarbamate and wherein the salt of dimethyldithiocarbamate is sodium dimethyldithiocarbamate.

10. The method of claim 9 wherein said weight ratio is about 1:1.

11. A dry water soluble microbiocide composition produced by the method of claim 7.

12. A dry water soluble microbiocide composition produced by the method of claim 10.

* * * * *